(12) United States Patent
Liu et al.

(10) Patent No.: US 8,512,322 B1
(45) Date of Patent: Aug. 20, 2013

(54) ANTIMICROBIAL LAYER FOR OPTICAL OUTPUT WINDOW

(75) Inventors: Harvey I. Liu, Fremont, CA (US); Robert E. Grove, Pleasanton, CA (US); Mark V. Weckwerth, Pleasanton, CA (US)

(73) Assignee: Tria Beauty, Inc., Dublin, CA (US)

( * ) Notice: Subject to any disclaimer, the term of this patent is extended or adjusted under 35 U.S.C. 154(b) by 242 days.

(21) Appl. No.: 12/772,104

(22) Filed: Apr. 30, 2010

Related U.S. Application Data

(60) Provisional application No. 61/174,936, filed on May 1, 2009.

(51) Int. Cl.
*A61B 18/20* (2006.01)

(52) U.S. Cl.
USPC .................................. 606/9; 606/15

(58) Field of Classification Search
USPC .................... 606/9, 15; 607/88–94
See application file for complete search history.

(56) References Cited

U.S. PATENT DOCUMENTS

| | | | |
|---|---|---|---|
| 4,232,678 A | 11/1980 | Skovajsa | 128/395 |
| 5,735,844 A | 4/1998 | Anderson et al. | 606/9 |
| 5,885,273 A | 3/1999 | Eckhouse et al. | 606/9 |
| 6,096,029 A | 8/2000 | O'Donnell, Jr. | 606/9 |
| 6,197,020 B1 | 3/2001 | O'Donnell, Jr. | 606/9 |
| 6,277,111 B1 | 8/2001 | Clement et al. | 606/9 |
| 6,508,813 B1 | 1/2003 | Altshuler | 606/9 |
| 6,888,661 B1* | 5/2005 | Islam et al. | 359/260 |
| 7,118,563 B2 | 10/2006 | Weckwerth et al. | 606/9 |
| 7,250,045 B2 | 7/2007 | Island et al. | 606/17 |
| 7,452,356 B2 | 11/2008 | Grove et al. | 606/9 |
| 7,824,023 B2 | 11/2010 | Izawa et al. | 347/85 |
| 2004/0039242 A1* | 2/2004 | Tolkoff et al. | 600/9 |
| 2008/0039768 A1* | 2/2008 | Francis | 604/8 |
| 2008/0125838 A1* | 5/2008 | Francis | 607/92 |
| 2009/0275933 A1* | 11/2009 | Zelickson et al. | 606/15 |
| 2010/0160904 A1* | 6/2010 | McMillan et al. | 606/16 |
| 2011/0152978 A1* | 6/2011 | Dacey et al. | 607/92 |
| 2011/0190749 A1* | 8/2011 | McMillan et al. | 606/16 |

OTHER PUBLICATIONS

Rao, et al., "Optical Properties of Electron-beam Evaporated TiO2 Films Deposited in an Ionized Oxygen Medium", Journal of Vacuum Science & Technology A: Vacuum, Surfaces, and Films, vol. 8, No. 4, pp. 3260-3264.

Wong, et al., "Visible-Light-Induced Bactericidal Activity of a Nitrogen-Doped Titanium Photocatalyst against Human Pathogens", Applied and Environmental Microbiology, pp. 6111-6116.

* cited by examiner

*Primary Examiner* — Bill Thomson
*Assistant Examiner* — Jeffrey Lipitz
(74) *Attorney, Agent, or Firm* — King & Spalding L.L.P.

(57) ABSTRACT

Light-source treatment devices such as dermatological or cosmetic devices include a skin contacting surface layer that is antimicrobial. The antimicrobial skin contacting surface layer enhances the cleanliness of the device and helps reduce infection and contamination risks associated with use of the devices, particularly where the treatment of multiple individuals occurs. The antimicrobial layer may be titanium dioxide.

19 Claims, 5 Drawing Sheets

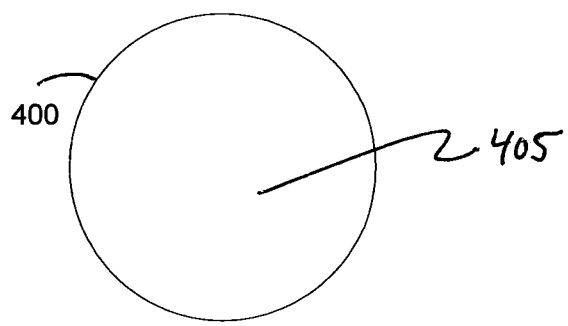
Figure 4A
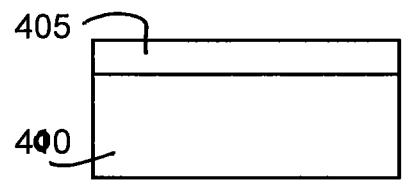
Figure 4B
Figure 4C
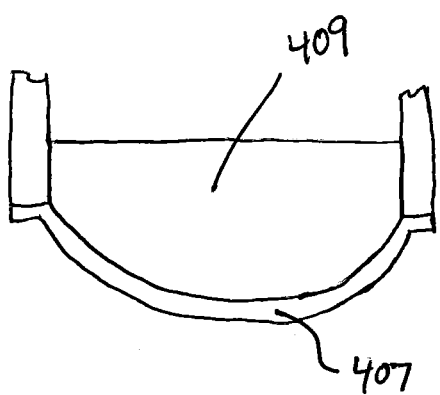

ANTIMICROBIAL LAYER FOR OPTICAL OUTPUT WINDOW

CROSS-REFERENCE TO RELATED APPLICATIONS

This application claims the benefit of U.S. Provisional Application No. 61/174,936 entitled "ANTIMICROBIAL LAYER FOR OPTICAL OUTPUT WINDOW" filed May 1, 2009, which is incorporated herein in its entirety.

FIELD OF THE INVENTION

The present invention relates to dermatologic treatment devices that deliver light from a light source through output windows, and more particularly, to treatment devices where the output windows are coated with a layer of a substance that reduces the risk of infection and contamination.

BACKGROUND OF THE INVENTION

The use of light sources, such as lasers and other high intensity light devices, for dermatologic treatment and cosmetic applications is well known in the art. For example, applications for these light based devices include, but are not limited to, epilation for the removal of unwanted hair, hair-regrowth inhibition, tattoo removal, treatment of birthmarks, acne treatment, and facial resurfacing.

Examples of light-based systems for dermatological treatment and cosmetic applications are described in U.S. Pat. Nos. 4,232,678; 5,735,844; 5,885,273; 6,096,029; 6,197,020; 6,277,111; 6,508,813; 7,118,563; 7,250,045; 7,452,356; and 7,824,023, the disclosures of which are hereby incorporated by reference.

In general, two types of light-based cosmetic and treatment devices are marketed. A first market segment includes devices that are sold to physicians and treatment facilities. Examples of such products include the LightSheer diode laser system, manufactured by Lumenis Ltd.; the SLP-1000 fiber-coupled diode laser, available from Palomar Medical Technologies Inc.; the Quantum flash lamp system, manufactured by Lumenis Ltd., and the CoolGlide Excel YAG laser, available from Altus Inc.

A second market segment includes light-based devices sold directly to end-user consumers. One such device is the TRIA Laser Hair Removal System, manufactured by TRIA Beauty, Inc. The TRIA system is a hand-held device with an optical output portion that is placed in contact with the epidermis. Light from a diode laser is delivered to the skin to remove unwanted hair.

Many of the light-based devices sold in both market segments contact areas of the skin during treatment. Light from the light-source may be delivered through a lens or other form of optical output window (e.g., the LightSheer system). The optical output window may have an outer surface that contacts the epidermis.

Optical windows generally are made from materials that are appropriate for the dermatologic and/or cosmetic applications. Materials may be used such as sapphire, which in general has a high heat capacity and high thermal diffusivity. Also, sapphire use is particularly suitable for dermatologic and cosmetic applications because the refractive index of sapphire is near the refractive index of skin. In general, less light is reflected back away from the skin at a boundary of sapphire and skin than at other boundaries where skin contacts a material with a retractive index greater than the retractive index of sapphire.

Titanium dioxide ($TiO_2$) has a refractive index between about 2.1 and 2.6. It is known that $TiO_2$ has a photochemical property that enables the decomposition of various harmful substances, such as organic chemicals and microorganisms. Such decomposition occurs by oxidation, when the sapphire is exposed to ultraviolet light (UV light) (e.g., from sunlight, from fluorescent light sources) and reactive oxygen species are formed. This antimicrobial property of $TiO_2$ can be further enhanced utilizing nitrogen doping. See M. Wong, et al., "Visible-light-Induced Bactericidal Activity of a Nitrogen-Doped Titanium Photocatalyst against Human Pathogens: Applied and Environmental Microbiology, p. 6111-6116, (September 2006).

The refractive index of $TiO_2$ substantially exceeds the refractive index of skin, which is between about 1.3 and 1.55. Thus, while it may be desirable in dermatologic and cosmetic applications to have a device with an antimicrobial surface such as $TiO_2$ in general, the presence of such skin contacting materials necessarily compromises the delivery of light to the skin.

SUMMARY OF THE INVENTION

The present invention provides an apparatus and method for the delivery of light-based energy through an antimicrobial layer in contact with the epidermis. The antimicrobial layer contacts the epidermis to enhance cleanliness and reduce the risk of infection and contamination associated with the device, particularly when the device is used on multiple individuals.

In accordance with a range of embodiments of the present invention, a titanium dioxide ($TiO_2$) layer coats a portion of a treatment device and forms a skin contact surface. In a preferred embodiment, the sapphire contact surface is generally flat.

In accordance with an alternate range of embodiments, a $TiO_2$ layer forms a skin contact surface that is curved. In a preferred embodiment, the sapphire contact surface is a generally convex skin contacting surface.

In accordance with a range of embodiments, the antimicrobial properties of the $TiO_2$ layer are enhanced using nitrogen doping. The $TiO_2$ layer may be applied using an activated reactive electron beam (e-beam) evaporation process.

An adhesion coating or layer also may be disposed between the antimicrobial layer and the substrate over which it is positioned.

The $TiO_2$ layer may be applied to a substrate positioned at least in part in the optical path of the light delivered to the skin. Thus, the $TiO_2$ material in part hinders the coupling of light into the skin, by increasing the opportunity for light to be reflected away from the skin and introducing loss into the optical system.

These and other attributes of the present invention may be better appreciated from the following description of the invention, together with the Figures.

BRIEF DESCRIPTION OF THE DRAWINGS

FIG. 4A is a frontal view of an exemplary circular, planar optical output window covered with an antimicrobial layer of the present invention.

FIG. 4B is a side view of the exemplary planar optical output window shown in FIG. 4A.

FIG. 4C illustrates application of an antimicrobial layer to a convex skin contacting surface.

DETAILED DESCRIPTION

Figure 1:
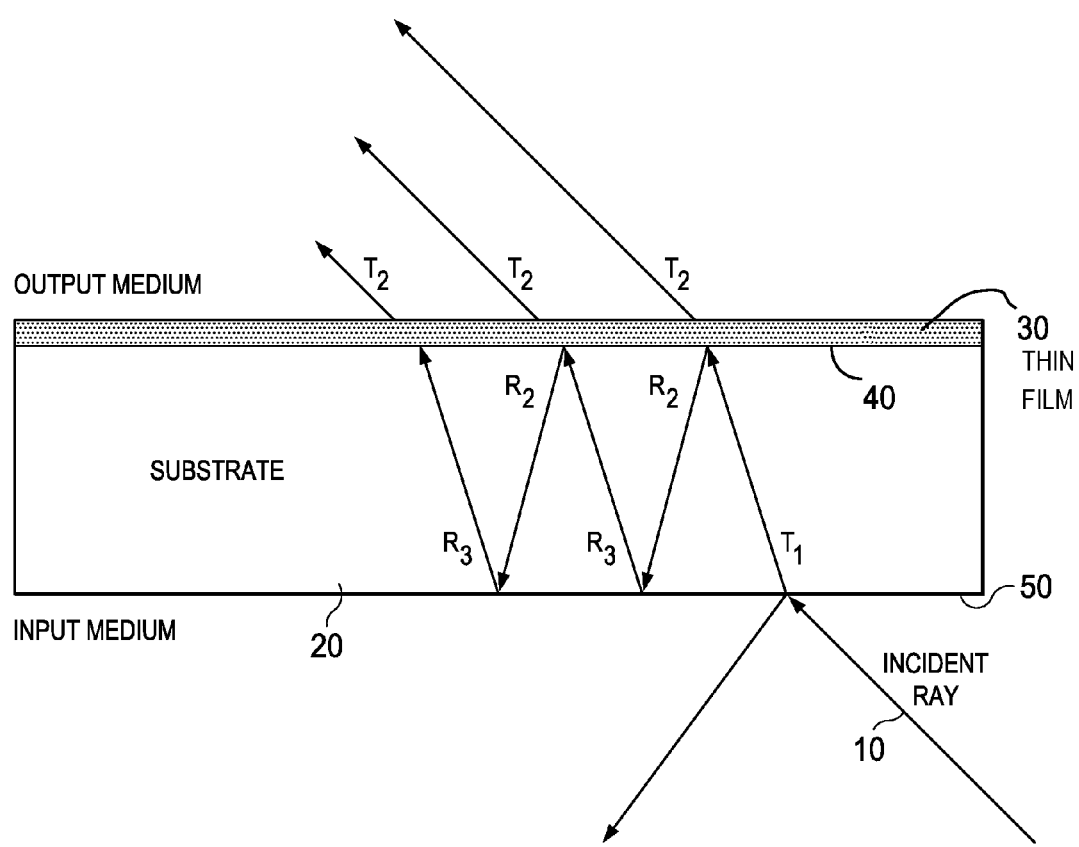
FIG. 1 illustrates the schematics of an exemplary light ray incident at an oblique angle onto a substrate coated with a thin layer of an antimicrobial substance.

Dermatologic and cosmetic light-source treatment devices include a skin contacting surface that is antimicrobial. The antimicrobial skin contacting surface comprises a layer that enhances the cleanliness of the device and reduces infection and contamination risks, particularly where the device is used to treat multiple individuals.

As used herein, the term "antimicrobial" refers to a material capable of destroying, preventing the development of or inhibiting the pathogenic activity of microorganisms, such as bacteria. The material itself may provide such results, or the material may play a role in the achievement of such results. For example, the material may promote the formation of reactive oxygen species. The material may be titanium dioxide ($TiO_2$) or zinc oxide (ZnO).

In accordance with a range of embodiments, $TiO_2$ may be deposited as a transparent layer on a substrate. At least a portion of the substrate may be positioned in the optical path of the dermatologic or cosmetic light-based treatment device.

In accordance with a range of embodiments, a transparent $TiO_2$ layer is applied as a layer across a sapphire substrate of a laser treatment device. For purposes of illustration only, and without limitation, the $TiO_2$ layer may be applied to the optical output windows of the laser treatment devices described in U.S. Pat. Nos. 7,452,356; 7,250,045; and 7,118,563.

The $TiO_2$ layer may be applied using a method that minimizes the Fresnel reflective losses at the boundaries between the sapphire substrate and the $TiO_2$ layer; and/or between the $TiO_2$ layer and the epidermal surface. A single layer high-refractive index $TiO_2$ layer may be provided on a lower-refractive index substrate, resulting in light transmission loss at the skin (e.g., a fluence reduction, a power density reduction).

Application of the $TiO_2$ layer to the substrate may be accomplished using an activated reactive electron beam (e-beam) evaporation process, although it will be recognized by those skilled in the art having the benefit of this disclosure that any deposition process producing a layer of desired thickness may be used.

In one e-beam evaporation process the $TiO_2$ compound is formed on a heated substrate by electron beam evaporation of TiO (Balzers) in an ionized oxygen medium produced by a cold cathode discharge. The layer may be applied so that the entire skin contacting surface of the device is covered, thereby ensuring that the entire surface in contact with the skin comprises antimicrobial material. FIGS. 4A and 4B, for example, illustrate application of an antimicrobial layer to a planar circular substrate to form an antimicrobial skin contacting surface. By way of further example, FIG. 4C illustrates application of an antimicrobial layer to a convex skin contacting surface.

Fresnel Reflection Calculation

For a light ray incident at a given angle $\theta_i$ relative to the material interface normal, the reflection and transmission intensity ratios are described by a set of basic Fresnel equations, as described for example by Simon Ramo, John R. Whinnery, and Theodore van Duzer, *Fields and Waves in Communication Electronics*, Chapter 6, 2nd Edition, John Wiley & Sons, Inc. (1984). The reflection (R) and the transmission (T) ratios are:

$$R = |\rho|^2 = \left|\frac{Z_L - \eta}{Z_L + \eta}\right|^2 \tag{1}$$

$$T = 1 - R \tag{2}$$

where $Z_L$ is the load field impedance transformed from the output side, and $\eta$ is the intrinsic impedance of the input medium.

The intrinsic impedance $\eta$ of a given medium with an oblique ray is given by the following equations for the two orthogonal polarization conditions.

$$\eta = \left(\frac{1}{n}\right)\cos(\theta_i) \tag{3}$$

$$\eta = \left(\frac{1}{n}\right)\sec(\theta_i) \tag{4}$$

where $\eta$ is the medium material refractive index, and $\theta_i$ is the ray angle in the medium relative to the interface normal.

The load impedance $Z_L$ is calculated by transforming the output medium intrinsic impedance $\eta_L$ from equation (3) and (4) through the intervening layers using the following equations.

$$Z_L = \eta_i \left[\frac{\eta_L \cos(\phi) + i\eta_i \sin(\phi)}{\eta_i \cos(\phi) + i\eta_L \sin(\phi)}\right] \tag{5}$$

where $\eta_i$ is the intervening layers' intrinsic impedance as described by the same equation (3) and (4) with difference refractive indices and ray angles, and $\phi$ is the propagation phase delay through the layer under consideration. It is worth noting that this is a complex number calculation as shown by the imaginary prefactor i in the equation.

The propagation phase factor $\phi$ is the phase number for the optical path length through the thin layer.

$$\phi = \frac{2\pi}{\lambda_O} n d \cos(\phi_i) \tag{6}$$

where d is the thin layer thickness, $\lambda_o$ is the free space wavelength for the light source, and $\eta$ is the layer refractive index.

The calculation of the internal ray angle $\theta_i$ follows the well known Snell's Law.

$$n_1 \sin(\theta_1) = n_2 \sin(\theta_2) \tag{7}$$

With equations (1) through (7), one can calculate the transmission and reflection intensity ratios at any dielectric interface. These equations were used to calculate the total transmission through a transparent dielectric substrate window coated with an antimicrobial layer on the output side (see FIG. 1). Due to the multiple internal reflections, the total net transmission ratio (T) through the coated window can be shown as follows.

$$T = T_1 T_2 \left( \frac{1}{1 - R_2 R_3} \right) \quad (8)$$

Each of the interface transmission and reflection ratios ($T_1$, $T_2$, $R_2$, $R_3$) was calculated individually using equations (1) through (7).

Referring now to FIG. 1, the schematics of an exemplary ray 10 incident at an oblique angle onto a thick optical window substrate 20 with its output side coated with a layer 30 of $TiO_2$ are shown. FIG. 1 demonstrates, among other things, the multiple bounces within the substrate 20 with internal reflection ratios of R2 at the output interface 40 and R3 at the input interface 50. T1 and T2 are the transmission ratios at the input interface 50 and the output interface 40, respectively.

Light Delivery

In accordance with a range of embodiments, a system is provided for use with a light source, such as an 800-nm laser input light source. The system includes a substrate of optically thick sapphire with a refractive index of about 1.76. The output side of the sapphire substrate is coated with a single layer $TiO_2$ thin hard layer, which has a refractive index of about 2.4.

The net output transmission of the system was calculated using equation (8), shown above, for four different combinations composed of two different input ray angular distributions (normal incidence single ray and Lambertian distribution rays), and two different output contact media (air with a refractive index close to 1, and skin with a refractive index close to 1.4). The Lambertian distribution was the cosine angular intensity distribution. In this case, the total output transmission was calculated by integrating equation (8) for each incidence angle with its cosine weighting factor.

Figure 2:
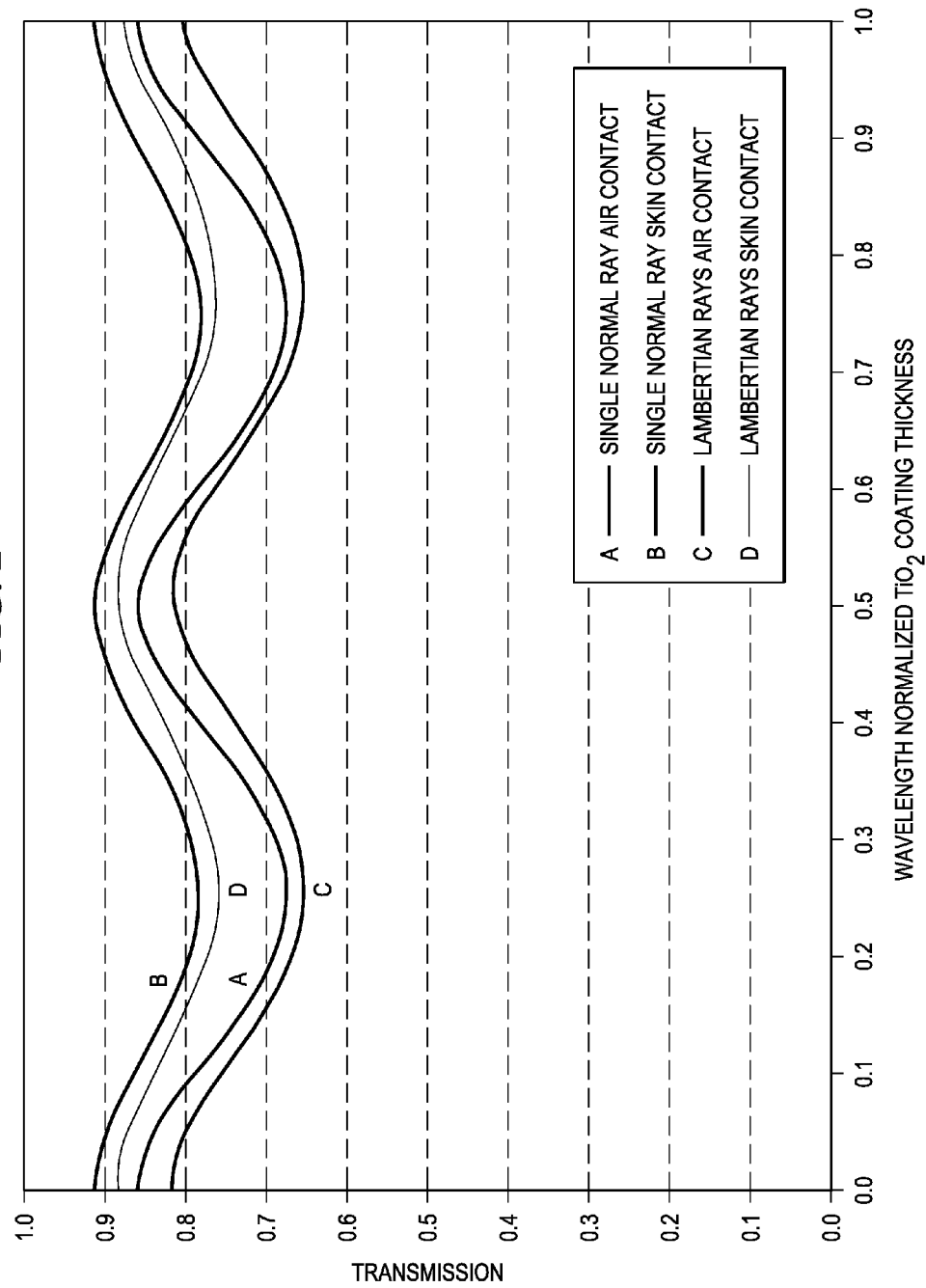
FIG. 2 illustrates exemplary light transmission patterns relative to the thickness of the preferred antimicrobial layer.

Total coated substrate transmission ratios were calculated for the four experimental conditions as a function of the wavelength normalized $TiO_2$ layer thickness on the output side. The results for the four experimental conditions are shown in FIG. 2. The curve labeled A represents a single normal incidence ray with the $TiO_2$ output surface contacting air. The curve labeled B represents a single normal incidence ray with the $TiO_2$ output surface contacting skin. The curve labeled C represents a Lambertian source with the $TiO_2$ output surface contacting air. The curve labeled D represents a Lambertian source with the $TiO_2$ output surface contacting skin. Layer thicknesses used were between about 100 nm to about 200 nm.

The $TiO_2$ layer thickness was normalized to the source wavelength in the material, which was equal to $\lambda_o/n_f$. In this case, $\lambda_o$ was the source free space wavelength of 800 nm, and $n_f$ was the $TiO_2$ refractive index of 2.4. The normalizing unity film thickness was (800/2.4)=333 nm.

As shown in FIG. 2, net transmission is higher when the $TiO_2$ output surface with a high index of refraction was in contact with a much lower refractive index material (e.g., skin). The Lambertian ray distribution involved a transmission decrease due to the inherently lower transmission of the oblique rays. Transmission with air contact was lower as compared to transmission with skin contact. However, all curves exhibited the same general transmission modulation pattern relative to the different layer thicknesses. In each case, net transmission may be optimized at the multiples of half material wavelength. For an 800-nm source, the $TiO_2$ (refractive index of about 2.4) half-wave layer thickness was about 167 nm. This half-wave layer thickness was also shown to be independent of the source wavelength. With a layer thickness of about 167 nm±20 nm, the refractive loss introduced by the inclusion of the high index layer of $TiO_2$ was minimized, while at the same time ensuring that the skin is contacted only by the $TiO_2$ and not by the sapphire.

For half-wave high refractive index layers using the sapphire/$TiO_2$ system described, a $TiO_2$ thin layer was deposited by reactive electron-beam evaporation of TiO (Balzers) onto a heated (80° C.) sapphire substrate in an ionized oxygen medium, according to the method described by K. Narashimha Rao and S. Mohan, in "Optical properties of electron-beam evaporated $TiO_2$ layers deposited in an ionized oxygen medium", Journal of Vacuum Science & Technology A: Vacuum, Surfaces and Films 8(4), p. 3260-3264 (1990).

Figure 3:
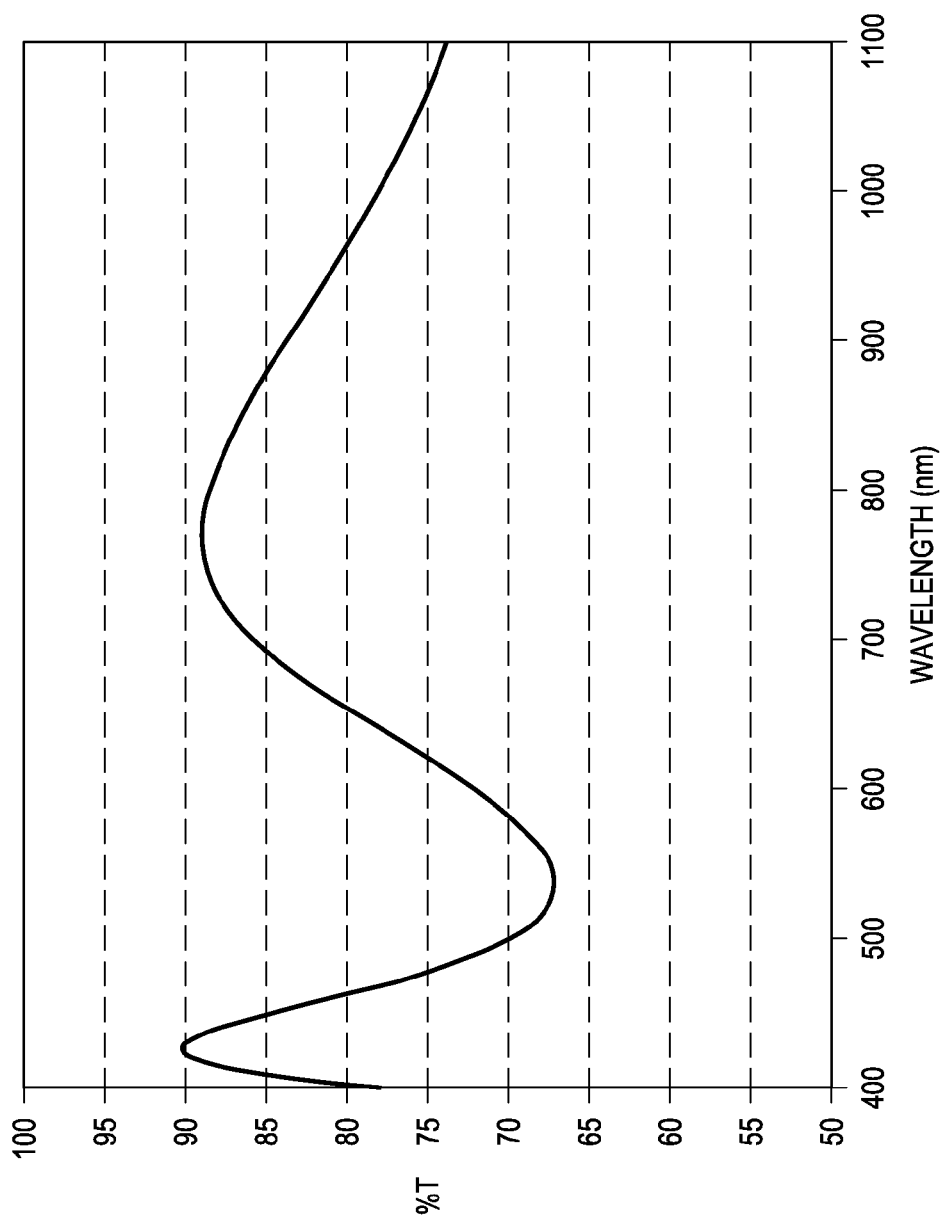
FIG. 3 illustrates exemplary transmission spectra from a half-wave $TiO_2$ layered optical window for a monochromatic light source.

In an alternative embodiment, a 5 nm thick SiO adhesion coating was applied to the sapphire substrate prior to deposition of the $TiO_2$ layer. The adhesion coating did not appear to reduce significantly the transmission as compared to the completed optical system with the sapphire substrate and the $TiO_2$ layer. The output transmission spectra were measured with a spectrophotometer and the results are shown in FIG. 3. The measured net transmission of 87% at 800-nm wavelength generally agrees well with the calculated value of 85% for normal incidence and air contact, with the variation likely due in large measure to the limitations of the measurement equipment and/or test set-up.

The embodiment of FIG. 3 was also tested using a Lambertian source (SpectraGenies iEpi hair removal device). No output loss was measured despite the high refractive index $TiO_2$ layer (again, likely due in large measure to the limitations of the measurement equipment and/or test set-up). Accordingly, a device including a high refractive-index antimicrobial optical layer as a skin contact surface may be optimized in part by minimizing the loss associated with the presence of the layer.

Figure 5:
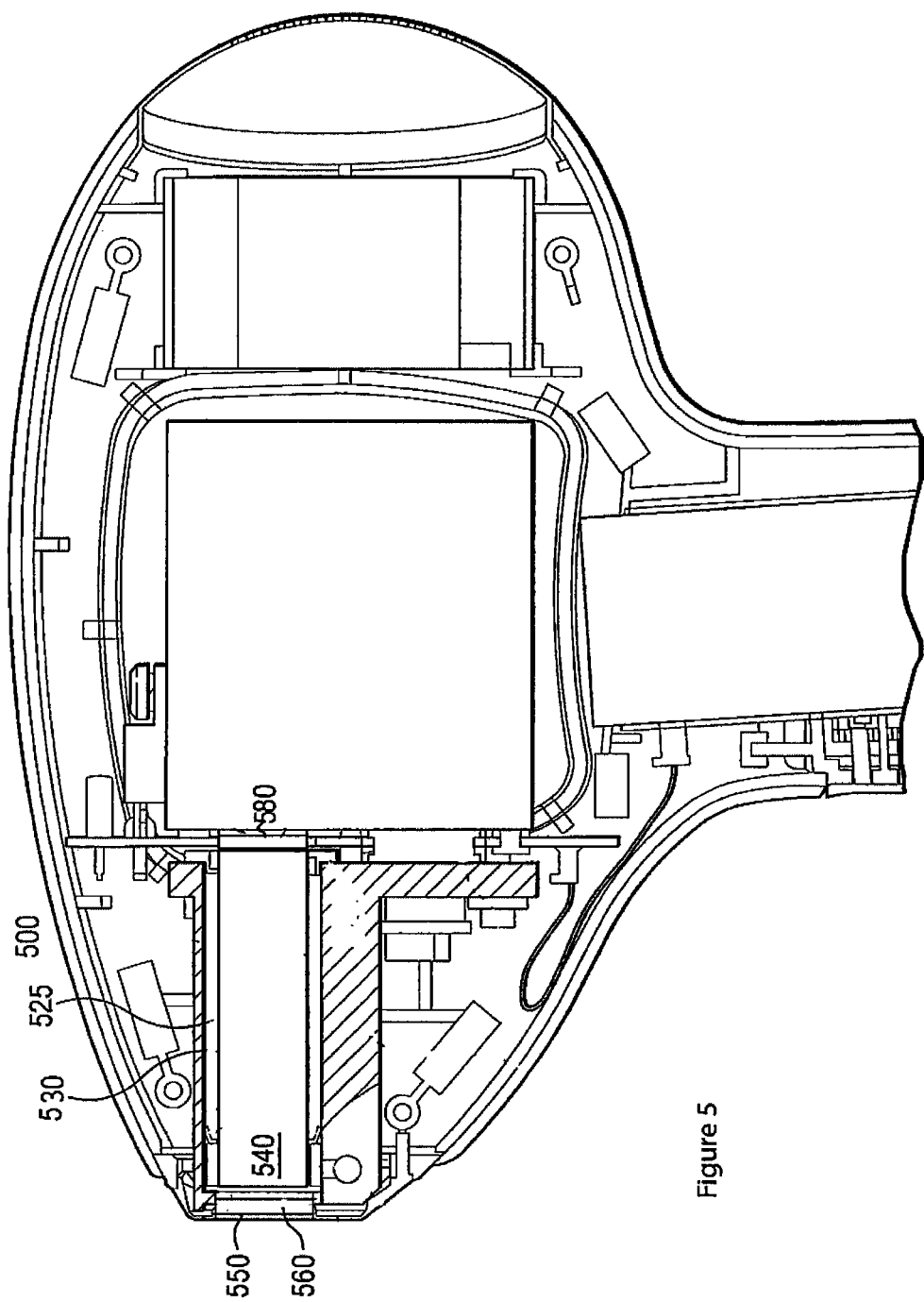
FIG. 5 illustrates an exemplary dermatologic treatment apparatus including an antimicrobial skin contacting surface.

Referring next to FIGS. 4A, 4B and 5, an exemplary substrate with an antimicrobial layer can be better appreciated. In FIG. 4A, the substrate 400 is shown in front plan view, while in FIG. 4B the substrate 400 is shown in side view. The antimicrobial layer 405 is shown relative to the substrate 400, which can be sapphire or other similar material. Referring next to FIG. 5, the installation of the substrate with the antimicrobial layer into a treatment device can be better appreciated. In particular, the device 500 includes a light source 580 which conveys light into a mixer 540 supported within a barrel 530. An air gap 525 may exist between the barrel and the mixer. Pressed, fixedly placed, or otherwise positioned into the front of the barrel 530 is the substrate portion 560. Covering the portion 560 is the antimicrobial layer 550, which forms the only surface of the device 500 that contacts the skin, thus promoting reduced infection and/or contamination that might occur from use of the device. It will be appreciated that, while the substrate shown in the illustrated embodiment of FIG. 5 is flat and lacks surface shape, a shaped layer or surface also may be used, including but not limited to a layer or surface applied to a convex substrate 409, in which case the antimicrobial layer 407 is also convex (see FIG. 4C).

Device optimization may depend upon the type of device. For example, a device which emits light continuously (i.e., non-pulsed light) may be optimized by increasing the intensity of the device light source in order to maintain at the skin a desired fluence. A device which emits pulsed light may be optimized by increasing the intensity of the light source, extending the pulse width, or some combination of both steps, to maintain at the skin a desired fluence or power density. Also, to maintain a desired power density at the skin, a reduced device output aperture or beam size may be used. In some cases, such optimization may occur during manufacture of the device as a result of calibration testing. For example, pulse width might be adjusted automatically in order to achieve a desired fluence for a device.

Devices including an antimicrobial layer as described herein may be characterized as less efficient due to a loss introduced by the presence of such a layer, or due to the nature of certain operational parameters when steps have been taken to reduce or minimize such a loss. For example, less efficient devices might dissipate more heat, use more battery power, produce more light, etc., as compared with other, more efficient devices. Accordingly, device optimization may involve the control of one or more of such operational parameters to achieve a desired device configuration or result.

Those skilled in the art having the benefit of this disclosure will recognize that other antimicrobial substances may be used alone or in combination with $TiO_2$ (e.g., zinc oxide (ZnO)). The substances may be applied or used in a variety of ways, e.g., in layer form, as particles embedded within layers or surfaces, as nano-particles, etc. Reactive oxygen species may be formed using the interaction of light (e.g., blue light having a wavelength of approximately 450-460 nm (e.g. 457 nm)) with appropriate substances (e.g., $TiO_2$, riboflavin, riboflavin-5 phosphate, etc.). Also, it will be similarly understood that the present invention is suitable for use with any light source (e.g., light emitting diodes (LEDs)), and is not limited to laser light sources. Further, the invention is useful with a wide variety of skin treatments or other treatment applications (e.g., hair removal, acne treatment, epilation for the removal of unwanted hair, hair-regrowth inhibition, tattoo removal, treatment of birthmarks, skin rejuvenation, wrinkle reduction, and facial resurfacing).

What is claimed is:

1. A dermatological device for treating skin comprising:
a light source configured to emit light at a wavelength $\lambda$;
a sapphire substrate; and
an antimicrobial layer disposed directly on a surface of the substrate, the antimicrobial layer positioned between the substrate and the skin during treatment, the antimicrobial layer having a refractive index n substantially different than a refractive index of skin, thus providing a refractive index mismatch between the antimicrobial layer and the skin;
wherein the antimicrobial layer has a thickness selected based on an integer multiple of a half-wave layer thickness defined by the equation:

half-wave layer thickness=½[$\lambda/n$], such that the selected thickness of the antimicrobial layer substantially minimizes refractive losses associated with the refractive index mismatch between the antimicrobial layer and the skin.

2. The dermatological device of claim 1, wherein the antimicrobial layer includes titanium dioxide.

3. The dermatological device of claim 1, wherein the antimicrobial layer includes zinc dioxide.

4. The dermatological device of claim 1, wherein:
the light source emits light at a particular visible wavelength; and
the antimicrobial layer includes at least one substance that forms a reactive oxygen species upon interaction with the particular visible wavelength.

5. The dermatological device of claim 4, wherein:
the light source emits blue light; and
the antimicrobial layer includes at least one substance that forms a reactive oxygen species upon interaction with blue light.

6. The dermatological device of claim 4, wherein the antimicrobial layer includes at least one of riboflavin and riboflavin-5 phosphate.

7. The dermatological device of claim 1, wherein the light source emits light at a visible wavelength.

8. The dermatological device of claim 7, wherein the light source emits light at a wavelength of approximately 800 nm or approximately 450-460 nm.

9. The dermatological device of claim 1, wherein the antimicrobial layer has a thickness of about 167 nm±20 nm.

10. The dermatological device of claim 1, wherein the antimicrobial layer is disposed directly on the substrate by an adhesion coating or layer between the substrate and the antimicrobial layer.

11. A dermatological device for treating skin, comprising:
a light source configured to emit light at a wavelength $\lambda$;
an output window optically coupled to the light source, the output window including:
a sapphire substrate; and
an antimicrobial layer formed over a surface of the substrate, the antimicrobial layer having a refractive index n substantially different than a refractive index of skin, thus providing a refractive index mismatch between the antimicrobial layer and the skin;
wherein the antimicrobial layer has a thickness selected based on an integer multiple of a half-wave layer thickness defined by the equation:

half-wave layer thickness=½[$\lambda/n$], such that the selected thickness of the antimicrobial layer substantially minimizes refractive losses associated with the refractive index mismatch between the antimicrobial layer and the skin.

12. The dermatological device of claim 11, wherein the light source emits light at a visible or near-infrared wavelength.

13. The dermatological device of claim 11, wherein the antimicrobial layer includes titanium dioxide.

14. The dermatological device of claim 11, wherein the antimicrobial layer includes zinc dioxide.

15. The dermatological device of claim 11, wherein:
the light source emits light at a particular visible wavelength; and
the antimicrobial layer includes at least one substance that forms a reactive oxygen species upon interaction with the particular visible wavelength.

16. The dermatological device of claim 15, wherein:
the light source emits blue light; and
the antimicrobial layer includes at least one substance that forms a reactive oxygen species upon interaction with blue light.

17. The dermatological device of claim 11, wherein the light source emits light at a wavelength of approximately 800 nm or approximately 450-460 nm.

18. The dermatological device of claim 11, wherein the antimicrobial layer has a thickness of about 167 nm±20 nm.

19. The dermatological device of claim 11, wherein the antimicrobial layer is disposed directly on the substrate.

* * * * *